United States Patent [19]

Choi

[11] Patent Number: 4,988,053
[45] Date of Patent: Jan. 29, 1991

[54] THERAPEUTIC WARMING BAG, AN APPARATUS FOR ITS MANUFACTURE, AND METHOD FOR MANUFACTURING A NEEDLE PUNCHED FABRIC OF THE BAG

[76] Inventor: Dong Sok Choi, Chungang Apt. Na-1206, Bangbae-Dong, Socho-ku, Seoul, Rep. of Korea

[21] Appl. No.: 294,883
[22] Filed: Jan. 9, 1989

[30] Foreign Application Priority Data

Jan. 12, 1988 [KR] Rep. of Korea .......................... 88-148
May 12, 1988 [KR] Rep. of Korea ........................ 88-6028

[51] Int. Cl.$^5$ ............................................ B65H 35/00
[52] U.S. Cl. ..................................... 242/56.8; 83/221; 83/222; 83/660
[58] Field of Search .................. 242/56.8; 83/221, 222, 83/283, 660, 244, 258

[56] References Cited

U.S. PATENT DOCUMENTS

| | | | |
|---|---|---|---|
| 248,623 | 10/1881 | Stuerholdt | 83/244 |
| 573,849 | 12/1986 | Belknap | 83/222 X |
| 1,633,718 | 6/1927 | Vold et al. | 83/221 X |
| 1,967,202 | 7/1934 | Dalton | 242/56.8 |
| 2,075,037 | 3/1937 | Hunter | 83/244 X |
| 2,381,322 | 8/1945 | Thomas | 242/56.8 |
| 3,146,283 | 8/1964 | DaValle | 242/56.8 X |
| 3,170,354 | 2/1965 | Scholl | 83/660 X |
| 3,490,664 | 1/1970 | Boultinghouse | 83/660 X |
| 3,513,738 | 5/1970 | Sheffer | 83/222 X |
| 3,566,726 | 3/1971 | Politis | 83/660 X |
| 3,976,049 | 8/1976 | Yamashita et al. | 126/263 |
| 4,268,272 | 5/1981 | Taura | 44/3 R |
| 4,657,531 | 4/1987 | Choi | 604/23 |

FOREIGN PATENT DOCUMENTS 57-14814  3/1982  Japan .
81-488  5/1981  Rep. of Korea .

Primary Examiner—John M. Jillions
Attorney, Agent, or Firm—Birch, Stewart, Kolasch & Birch

[57] ABSTRACT

A therapeutic warmer composed of a non-ventilative envelope and a film-coated bag disposed within the envelope wherein the film-coated bag includes a plurality of needle apertures disposed therein and further includes an exothermic composition and a mugwart powder whereby when the envelope is broken, and the contents are kneaded, heat is generated for warming the bag to use in warming and treating regions of the human body; a punching apparatus for adjustably forming the needle apertures so as to correspond with demand of the user; and also a method for manufacturing a punched fabric of the warming bag.

4 Claims, 5 Drawing Sheets

|   | Number of needle holes/cm² |
|---|---|
| A | 30 |
| B | 60 |
| C | 90 |
| D | 120 |
| E | 150 | ized
THERAPEUTIC WARMING BAG, AN APPARATUS FOR ITS MANUFACTURE, AND METHOD FOR MANUFACTURING A NEEDLE PUNCHED FABRIC OF THE BAG

BACKGROUND OF THE INVENTION

1. Field of the Invention

The present invention relates to a therapeutic warming bag for use in warming and treating regions of the human body, an apparatus for its manufacture, and a method for manufacturing a needle punched fabric of the bag, and more particularly, to a warmer which includes an exothermic composition consisting of iron powder, activated carbon, zeolite, and mugwart powder that may be exposed to the atmosphere for generating heat in an inner bag which is composed of a woven fabric or a non-woven fabric having a non-ventilative resin film coated on the one side thereof wherein the coated film contains a plurality of needle apertures; to a punching apparatus for forming the plurality of needle apertures in the coated resin film of the inner bag; and to a method for manufacturing the needle punched fabric of the bag.

2. Description of the Prior Art

Many types of warming bags heretobefore been proposed but in general have either been unsatisfactory or have required the development of a relatively complicated manufacturing process for achieving satisfactory results. For example, such warming bags contain an exothermic metal and a reaction assistant therein separated from each other by a partition. When it is to be used, the partition is torn and the contents are shaken and kneaded so as to mix. However, the mixing may be insufficient, the period of heat generation time may be reduced, and the torn portion may extend to the outer portion of the inner bag so that the contents spill out. Such devices are more particularly described in Korean Patent publication Nos. 78-549 and 81-488, and Japanese laid-open publication No. S053-34,187. Also such warming bags are composed of a non-ventilative outer bag and an inner bag having several ventilating apertures disposed within the outer bag wherein the inner bag contains exothermic contents. When it is to be used, the outer bag is broken and shaken to generate heat. However, such devices cannot control the heat-generated temperature and the warming period time thereof since the ventilating apertures disposed in the inner bags are not of sufficiently high number and the properties of the ventilating apertures cannot be immediately controlled according to demand of the user. Such devices are particularly mentioned in U.S. Pat. Nos. 3,301,250, 3,976,049 and 4,268,272, and Japanese publication No. S057-14,814.

SUMMARY OF THE INVENTION

Accordingly, it is an object of the present invention to provide an improved therapeutic warming bag which accommodates an exothermic composition and mugwart powder therein that may be exposed to the atmosphere to generate heat.

Another object of the present invention is to provide a therapeutic warmer composed of a non-ventilative outer bag and an inner bag disposed within the outer bag wherein the inner bag is made of a woven fabric or a non-woven fabric coated with a non-ventilative resin film disposed on one side of the coated fabric contains a plurality of needle apertures the number and size of which are controlled for achieving the goals of the user.

A further object of the present invention is to provide a punching apparatus for forming needle apertures on a coated woven fabric or a non-woven fabric to be manufacture on an inner bag which contains exothermic contents which generate heat when exposed to the air and mugwart powder wherein the apparatus includes a driving shaft connected to a clutch motor and a driving roller operatively connected to the driving shaft through a ratchet and connected to a press roller.

Still another object of the present invention is to provide a method for manufacturing a needle punched fabric of a warming bag which comprises introducing a fabric coated with film thereon from a supply coil to a punching body, punching the fabric with needles for forming needle apertures, and winding the punched fabric on a winding drum for use in manufacturing the warming bag.

Yet another object of the present invention is to provide a therapeutic warmer that is simple in construction, economical to manufacture, easily manipulated, and attractive in appearance.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a therapeutic warmer composed of a non-ventilative envelope and a film-coated bag disposed within the envelope wherein the film-coated bag includes a plurality of needle apertures disposed therein and further includes an exothermic composition and mugwart powder whereby, when it is to be used, the envelope is broken, and the contents are kneaded, heat is generated for warming the bag to use in warming and treating regions of the human body; and to a punching apparatus for adjustably forming the needle apertures so as to correspond with the demand of the user, and also a method for manufacturing a punched fabric of the warming bag.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
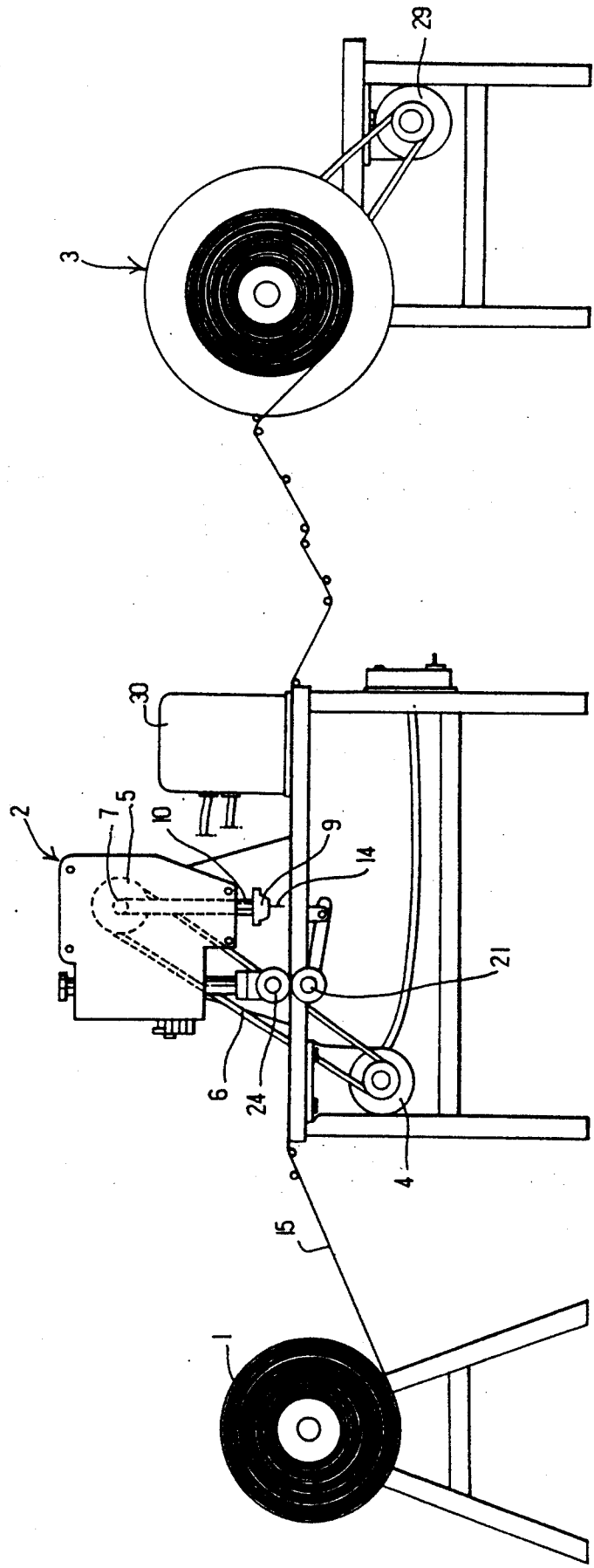
FIG. 1 is a front view of an apparatus according to the present invention.
Figure 2:
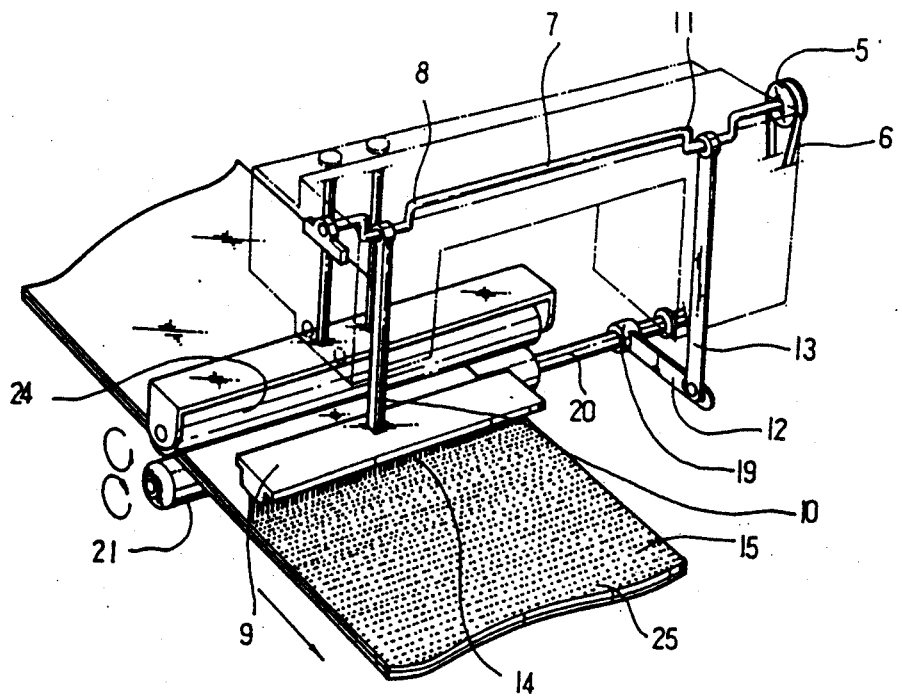
FIG. 2 is an enlarged perspective view of a punching body member of the apparatus according to the present invention.
Figure 8A:
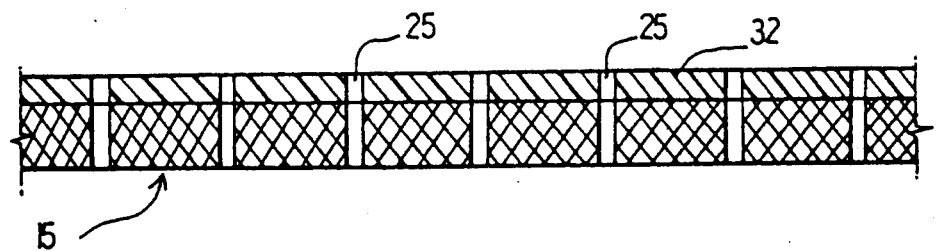
FIGS. 8(A), 8(B), and 8(C) are sectional views of a therapeutic warming bag according to the present invention.

Referring now in detail to the drawings for the purpose of illustrating preferred embodiments of the present invention, the punching apparatus as shown in FIGS. 1 and 2 comprises a supply coil 1, a needle body member 2, and a winding drum 3 for punching a coated woven or a coated non-woven fabric 15 to form a plurality of needle apertures 25 disposed in the fabric 15 while the fabric 15 is passing through the punching body member 2 from the supply coil 1 to the winding drum 3. The coated woven or the coated non-woven fabric 15 is coated by a non-ventilative resin film 32 thereon as follows as shown in FIG. 8(A):

A woven fabric or a non-woven fabric 15 is coated by a non-ventilative resin film 32 on the one side thereof through conventional devices such as a cooling cylinder having a miller, a semimeter, and a meter, and a conventional press roller made of a silicone rubber. At this time, the thickness of the coated film layer disposed on the fabric 15 is about 50 μm which is formed by repeating the coating process.

Figure 3:
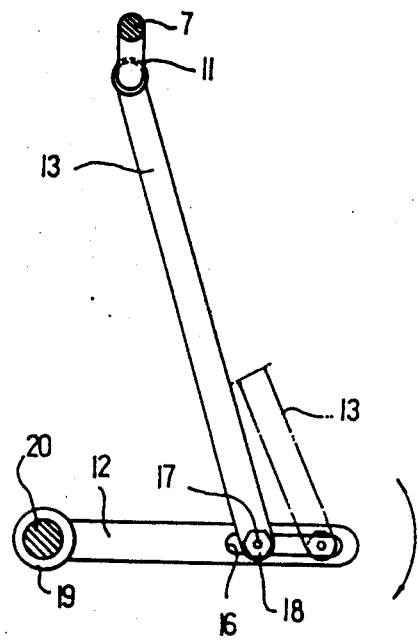
FIG. 3 is a exploded front view of second connecting rod of the punching body member of the apparatus according to the present invention.
Figure 4:
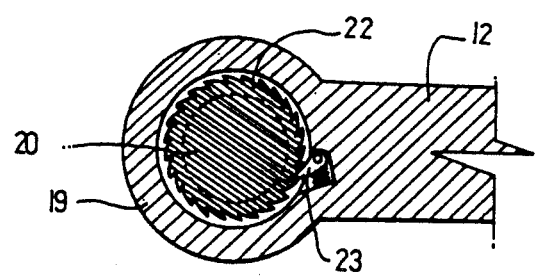
FIG. 4 is a cross-sectional view of a clutch end of a clutch rod of the apparatus according to the present invention.

As shown in FIGS. 1, 2, and 3, the punching body member 2 comprises a driving wheel 5 driven by first clutch motor 4 (1,700 r.p.m.) through a belt 6 and first connecting rod 10 rotatably connected to first crank 8 of a driving shaft 7 of the driving wheel 5 at the one end thereof. The punching body member 2 further comprises a needle punch 9 connected to the first connecting rod 10 at the other end thereof, second connecting rod 13 rotatably connected to second crank 11 of the driving shaft 7 at the one end thereof, and a clutch rod 12 pivotably connected to the second connecting rod 13 at the other end thereof.

The needle punch 9 includes a plurality of needles 14 each having a length of 0.01–0.1 mm for forming a plurality of needle apertures 25 disposed in the fabric 15. The second connecting rod 13 is connected to a bolt 17 which is adjustably mounted to a rectangular aperture 16 disposed in one portion of the clutch rod 12 through a nut 18 (FIG. 3). That is, when the second connecting rod 13 is mounted adjacent to the driving roller shaft 20, the rotating angle of the driving roller 21 is larger than when the second connecting rod is mounted to the opposite side of the driving roller 21 as indicated by the second connecting rod 13 (dashed line) of FIG. 3.

The clutch rod 12 is provided with a ring 19 for receiving a driving roller shaft 20 of a driving roller 21. The driving roller 21 is intermittently rotated by actuating a ratchet 22 and a stopper 23 since the second connecting rod 13 is converted to the intermittent rotation of the driving roller 21.

Figure 6:
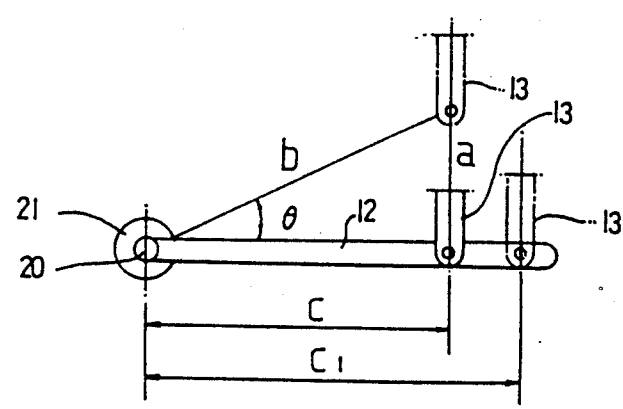
FIG. 6 schematically shows main components of the apparatus according to the present invention.

As shown in FIG. 6, the amount of fabric 15 produced can be represented by the following equation:

$$L = N \cdot P$$

$$L = N\pi D$$

$$N = \frac{\cos\theta \cdot M}{360}$$

-continued
$$L = \frac{\cos\theta \cdot M}{360} \pi D$$

$$l = \frac{\cos\theta}{360} \pi D \cdot M = L$$

wherein
L is the produced amount (m/min),
N is the number of rotations of the driving roller 21,
D is a diameter of the driving roller 21,
P is the circumference of the driving roller 21,
M is r.p.m. of the clutch motor 4,
l is a length of the lead, and
C is the length of the clutch rod 12.

Figure 8B:
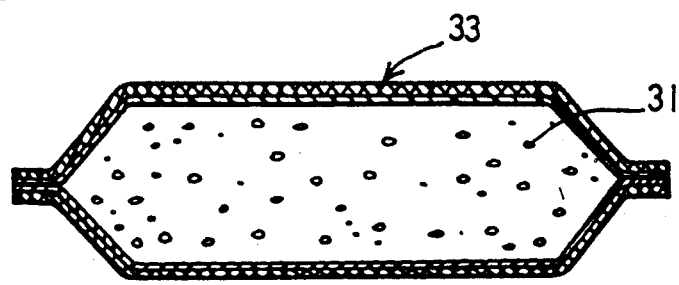
Figure 8C:
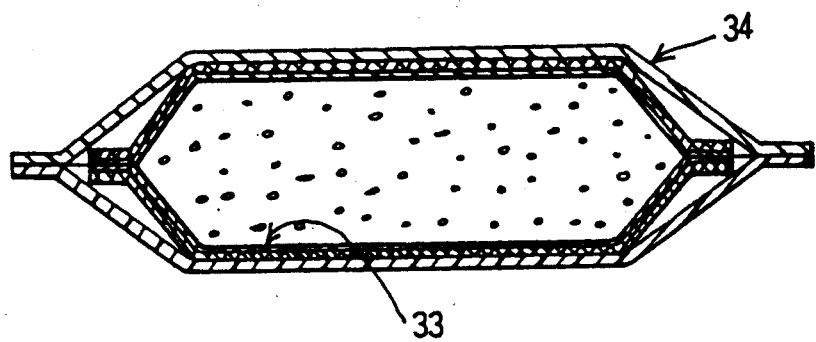

Therefore, when the length of the clutch rod 12 is smaller, the COS θ is larger so that the length of L and l is bigger. That is, when the second connecting rod 13 is adjustably moved within the rectangular aperture 16 disposed in the end portion of the clutch rod 12, the produced amount can be controlled and the mutual distance of the longitudinal needle lines can be easily controlled to correspond with the specific desired properties of the warming bag 33 as shown in FIGS. 8(A), 8(B), and 8(C). Since the driving roller 21 is suddenly stopped when the needle punch 9 comes down, the coated fabric 15 is punched by the plurality of needles 14 (FIG. 2). In turn, since the driving roller 21 is rotated when the needle punch 9 comes up, the coated fabric 15 is delivered therebetween.

Figure 5A:
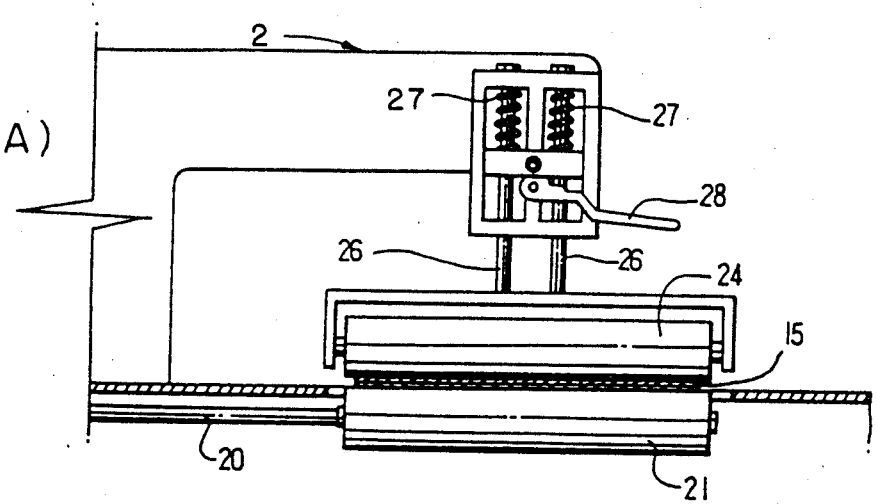
FIG. 5(A) and 5(B) are front views of a driving roller and a press roller of the apparatus according to the present invention.
Figure 5:
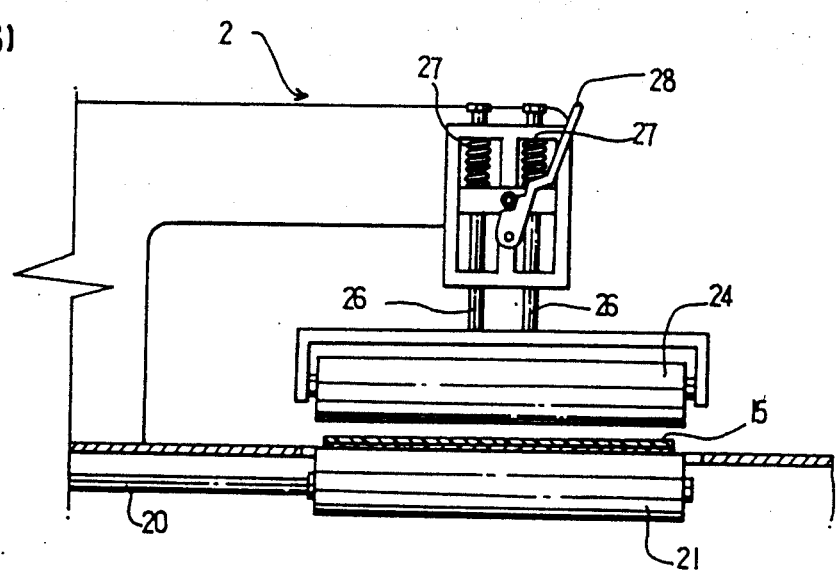

As shown in FIGS. 5(A) and 5(B), a press roller 24 mounted to a pair of rods 26 is closely positioned over the driving roller 21 for passing therethrough the fabric 15 to be punched. The pair of rods 26 are wound along springs 27 for the operation of the down movement of the press roller 24 to effectively deliver the fabric 15 between the press roller 24 and driving roller 21. The punched and delivered fabric 15 is taken up the winding drum 3 by actuating a D.C. motor 29. The rotating speed of the winding drum 3 is the same as that of the driving roller 21 since a D.C. motor controller 30 can be controlled automatically.

A method for manufacturing the warming bag 33 is as follows:

The coated woven or coated non-woven fabric 15 is wound along the supply coil 1 and is delivered to the punching body member 2. While the coated fabric 15 is passing between the press roller 24 and the driving roller 21, the needle punch 9 punches the fabric 15 by the up and down movement thereof. The punched and coated fabric 15 is wound along the winding drum 3.

As shown in FIGS. 8(A), 8(B), and 8(C), the coated and punched fabric 15 having the non-ventilative resin film layer 32 and the plurality of needle apertures 25 can be used to make the fabric bag 33. The fabric bag 33 contains exothermic materials 31 such as iron powder, activated carbon, zeolite, and mugwart powder, and the like for generating heat when exposed to the atmosphere. The fabric bag 33 containing the exothermic materials 31 is inserted into a non-ventilative envelope 34. When it is to be used, the non-ventilative envelope 34 is broken and air is immediately introduced into the inner portion of the bag 33 so that the exothermic materials 31 generate heat to warm the bag 33 for warming and treating the regions of the human body.

Figure 7:
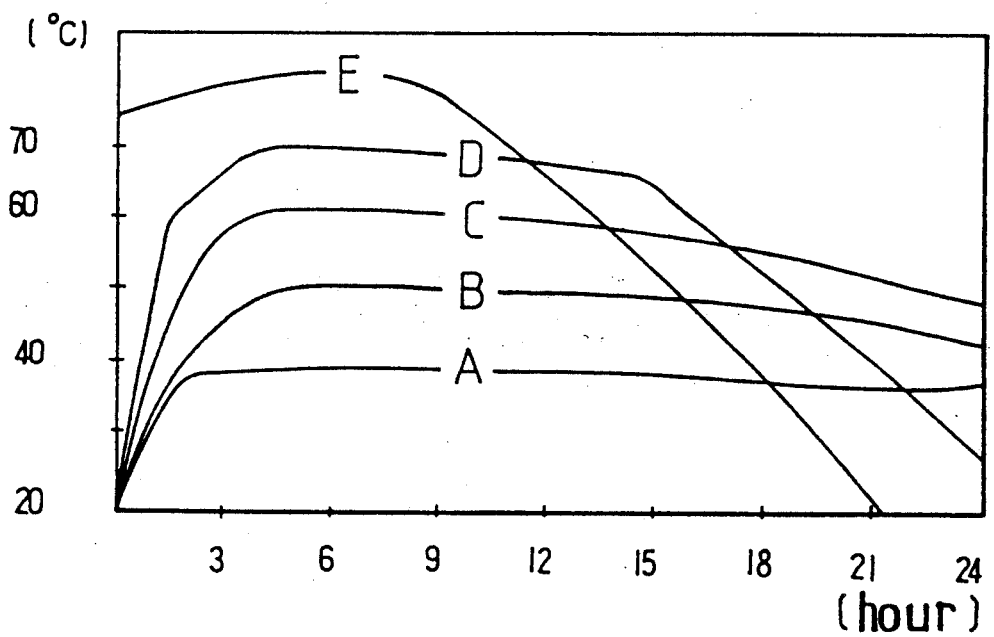
FIGS. 7(A) and 7(B) graphically show exothermic temperatures over periods of time.

Referring to FIGS. 7(A) and 7(B), there are graphically illustrated exothermic temperatures over warming periods of the bag 33. The data is obtained by the use of the fabric 15 which has a plurality of needle apertures for controlling the amount H of oxygen at 1-600 cc/min per cm². As shown in FIGS. 7(A) and 7(B), when the number of needle apertures is 30, the warming period of time is longest. However, the exothermic temperature gradually increases and the warming period time gradually shortens when the number of the needle apertures are 60, 90, 120, and 150.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. An apparatus for manufacturing a punched fabric for use in a therapeutic warming bag which comprises:
   a supply coil for supplying a film coated fabric,
   a punching body member for punching said film coated fabric to form a plurality of needle apertures disposed in the film coated fabric, said punching body member including:
      a driving wheel driven by a motor,
      a driving shaft extending to a shaft of said driving wheel, said driving shaft having a pair of first and second cranks,
      a first connecting rod rotatably connected to said first crank at the one end, and connected to a needle punch at the other end thereof, said needle punch having a plurality of needles for forming said needle apertures,
      a second connecting rod rotatably connected to said second crank at the one end, and adjustably connected to a clutch rod at the other end thereof through adjusting means for controlling the number of needle apertures in the coated fabric, said clutch rod intermittently rotatably connected to a driving roller shaft through a ratchet and a stopper,
      a driving roller having said driving roller shaft for advancing the punched fabric, and
      a press roller having an operating switch for being operatively associated with said driving roller to effectively advance the punched fabric, and
      a winding drum for winding the punched fabric, whereby the needle punch punches while the driving roller is stopped, the apparatus forms the needle apertures in the coated fabric as desired.

2. The apparatus of claim 1, wherein the means for adjusting includes a rectangular aperture disposed in one end portion of the clutch rod, and a hole disposed in the other end of the second connecting rod for tightly engaging with a bolt and a nut.

3. The apparatus of claim 1, wherein the ratchet is formed on the driving roller shaft and the stopper is located in a recess disposed in an internal surface of the other end of the clutch rod.

4. The apparatus of claim 1, wherein the fabric is a woven fabric or a non-woven fabric.

* * * * *